United States Patent [19]

Span

[11] Patent Number: 4,459,485
[45] Date of Patent: Jul. 10, 1984

[54] GAMMA TOMOGRAPHY APPARATUS COMPRISING A PARALLELOGRAM SUSPENSION SYSTEM

[75] Inventor: Francis J. Span, Eindhoven, Netherlands

[73] Assignee: U.S. Philips Corporation, New York, N.Y.

[21] Appl. No.: 380,166

[22] Filed: May 20, 1982

[30] Foreign Application Priority Data

May 29, 1981 [NL] Netherlands ................. 8102616

[51] Int. Cl.³ .............................................. G01T 1/20
[52] U.S. Cl. .............................................. 250/363 S
[58] Field of Search .................................. 250/363 S

[56] References Cited

U.S. PATENT DOCUMENTS 2,967,939 1/1961 Caha ........................... 250/361 R
4,057,726 11/1977 Jaszczak ..................... 250/363 S
4,216,381 8/1980 Lange .......................... 250/363 S Primary Examiner—Janice A. Howell
Assistant Examiner—Constantine Hannaher
Attorney, Agent, or Firm—Marc D. Schechter

[57] ABSTRACT

In a radiation apparatus an element, which is carried by a balanced suspension system, is to be positioned relative to an object. The element and a counterweight are carried by a parallelogram suspension system in order to increase the adjusting accuracy and the freedom of movement. In order to obtain a smooth, static movement, even during rotation of the entire suspension system, the positioning function and the supporting function of one of the pivotal supports are separated, each function being performed by a separate pivot.

6 Claims, 8 Drawing Figures

GAMMA TOMOGRAPHY APPARATUS COMPRISING A PARALLELOGRAM SUSPENSION SYSTEM

BACKGROUND OF THE INVENTION

The invention relates to a radiation apparatus comprising an element which is to be positioned with respect to an object. The element to be positioned is supported by a balanced suspension system comprising a counterweight.

Such an apparatus which comprises a gamma camera as a detector element is known from U.S. Pat. No. 4,057,726. The gamma camera included in the apparatus described therein is rotatable with respect to an isocentric axis of a patient. It is usually desirable that the gamma camera also be radially movable with respect to the isocentric axis. Because a gamma camera in combination with a collimator coupled thereto is a comparatively heavy element, it is suspended in a balanced manner by means of a counterweight. In practice, measurements are often impeded by the counterweight, which necessarily also rotates about the patient. Apart from the necessarily heavy construction, this drawback is even greater when an apparatus is to be constructed so that all parts of a patient can be reached thereby.

SUMMARY OF THE INVENTION

It is an object of the invention to mitigate these drawbacks. To this end, in an apparatus according to the invention the suspension system comprises a parallelogram structure. From opposite ends of the parallelogram structure the element to be positioned and a counterweight are suspended via pivotal supports so as to balance one another.

In an apparatus according to the invention, the counterweight may be accomodated in a cabinet from which only a comparatively long arm projects. The long arm supports the element to be positioned and can be easily moved by hand both rotationally and radially with respect to an object arranged on a supporting table. Due to the parallel suspension system, the detector plane of the gamma camera remains oriented in mutually parallel planes during radial movement.

In a preferred embodiment according to the invention, the moment arm of the counterweight is so short that the entire rotation mechanism and the counterweight can be accomodated in a comparatively narrow closed cabinet. The apparatus thus acquires a more attractive appearance. The appearance is even further enhanced because an opening is no longer required in the cabinet for the object. An inlet and outlet duct for a fluid to be used during the measurement can then be arranged near the axis.

In a preferred embodiment, one of the pivotal supports in the parallelogram suspension system has a double construction so that the construction is simplified, and the second arm for the element to be positioned no longer has a supporting function, so that the second arm may be of a light construction.

In a further prepared embodiment, a pivot point for the nonsupporting arm is shifted backward with respect to the element so that more free space for the object is obtained.

The rotation mechanism for the above embodiments may comprise a ring or a shaft or a combination of both.

The invention can be used not only for apparatus comprising a gamma camera as a detector but also in, for example, radiation apparatus comprising a heavy radiation source to be balanced, in simulators and in X-ray diagnostic apparatus comprising a rotatably arranged X-ray image intensifier as a detector with a balanced suspension system. In apparatus comprising two measuring heads or one radiation head and one measuring head, the invention can be used separately for both heads in order to avoid the drawback of imbalance which occurs when the adjustment of the heads is not the same.

BRIEF DESCRIPTION OF THE DRAWING

FIGS. 3a–3c schematically show three rotation mechanisms for an apparatus according to the invention, comprising a ring, a shaft and a combination thereof, respectively.

DESCRIPTION OF THE PREFERRED EMBODIMENTS

Figure 1A:
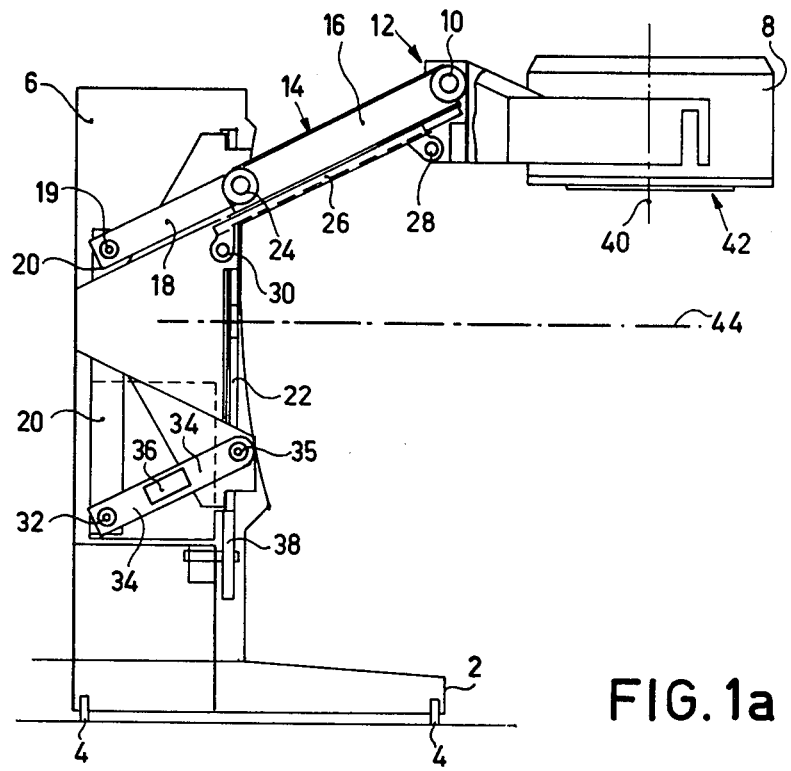
FIG. 1a schematically shows a preferred embodiment of an apparatus according to the invention which comprises a gamma camera carried by a balanced suspension system.
Figure 1B:
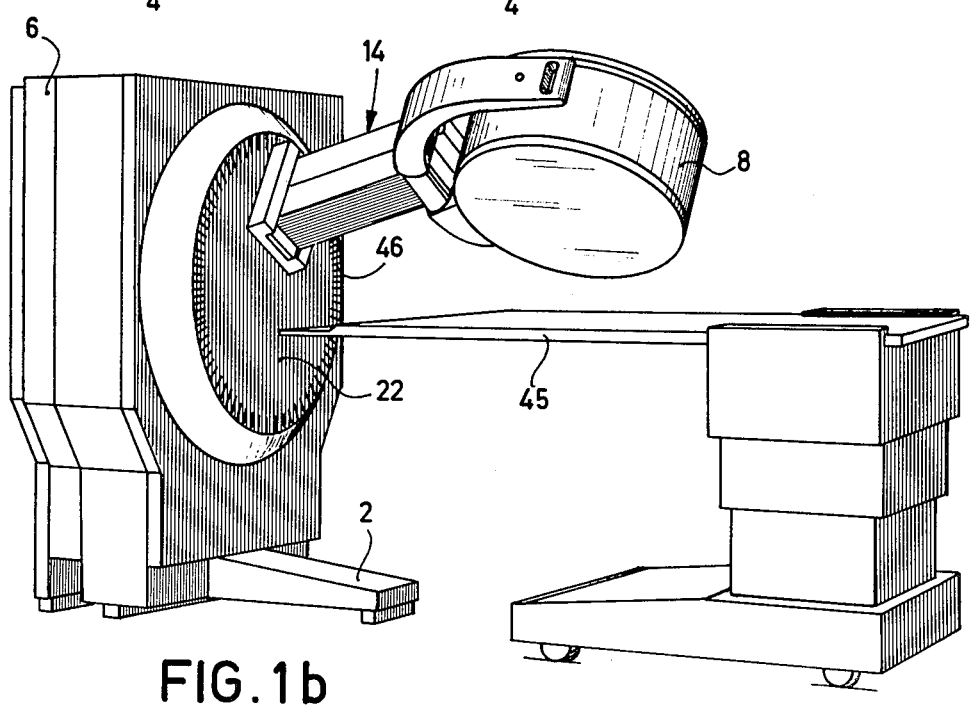
FIG. 1b is a perspective view of the apparatus according to the invention.

The apparatus shown in FIG. 1 comprises a base 2 which may comprise rollers 4, but which may also alternatively be rigidly connected to the floor. The base 2 supports a housing 6 which is shown in a partly open condition and which accomodates a suspension system for a gamma camera 8.

Via a pivot 10, the gamma camera 8 is suspended from a supporting device 12. Supporting device 12 comprises a first arm 14 which consists of two sections. A first arm section 16 of the arm 14 extends outside of the housing 6 and supports the gamma camera 8 via the pivot 10. A second section 18 of the arm 14 extends within the housing 6 and is connected at its end to a rod 20 by a pivot 19. A pivot 24 which is mounted on a supporting ring 22 interconnects the two sections of arm 14.

A second arm 26 (a control arm) is connected at one end to the gamma camera via a pivot 28 and at the opposite end to a pivot 30 which is mounted on the support ring 22. The rod 20 is connected via a pivot 32 to one end of a supporting arm 34. The other end of supporting arm 34 is connected to the supporting ring 22 by a pivot 35. To the supporting arm 34 there is secured a counterweight 36 which is shown as a comparatively small block for the sake of simplicity but which may be made of, for example, heavy segments (which may include rod 20 and arm 34). In this embodiment, the supporting ring 22 bears rotatably on, for example, two guide wheels 38 connected to the housing.

Due to the above-described balanced suspension system, the gamma camera 8 can be very easily moved by rotation of the arm 14 about the pivot 24, even when the arm 12 is comparatively long so that the camera 8 is spaced far from the housing 6. In practice, the distance between the near side of the housing 6 and the central axis 40 of the camera 8 will be approximately 1 m, so that a patient can be completely covered by measurement in two positions. Due to the double construction of the arms 12 and 26 a measuring entry face 42 of the camera is always parallel to a central axis 44, which is the axis of rotation of the supporting ring 22. Normally a patient is positioned so that this axis 44 is the isocentric axis for the patient during measurement. The patient usually rests on a patient table 45 (shown in FIG. 1b) which is independently displaceable and adjustable.

Figure 2A:
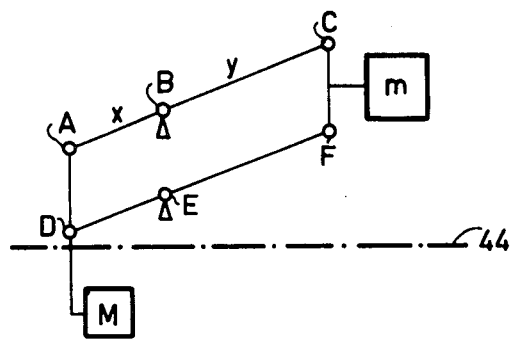
FIGS. 2a–2c schematically show three embodiments of parallelogram suspension systems.
Figure 2B:
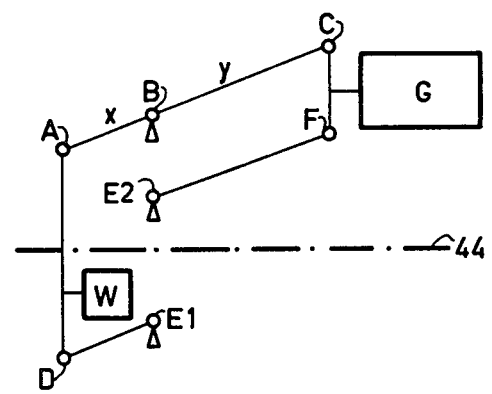
Figure 2C:
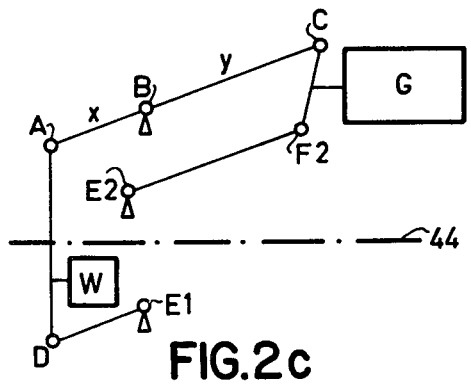
Figure 2C:
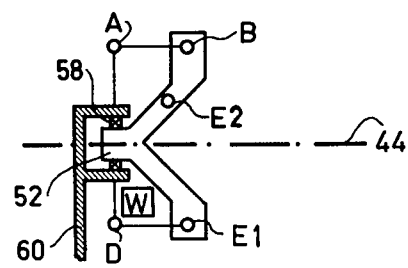

FIGS. 2a–2c schematically show, for the sake of clarity, three embodiments of a balanced parallelogram suspension system. The balance between the masses M and m is maintained as long as Mx=my.

During pivoting about points B and E (FIG. 2a), the points C and F move with one another between mutually parallel planes, so that an element secured thereto maintains a fixed orientation with respect to the axis of rotation 44 during the pivoting movement.

FIG. 2b shows an arrangement in which a supporting point E has a double construction such that the two functions of the point E, namely supporting and pivoting, are separated. The arm E2-F serves only for positioning the gamma camera G. The point E1 provides support for the counterweight W, so that a much higher degree of freedom is obtained. The structure is thus statically defined and the arm E2-F may have a thin construction so that more free space for the patient is obtained.

Even more free space is obtained for the patient by shifting the pivot E2 further to the rear with respect to G, so that this pivot can be situated completely inside the housing, as shown in FIG. 2c.

Figure 3A:
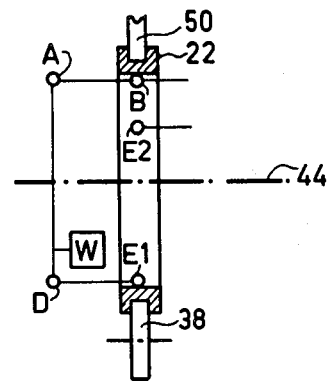
Figure 3B:
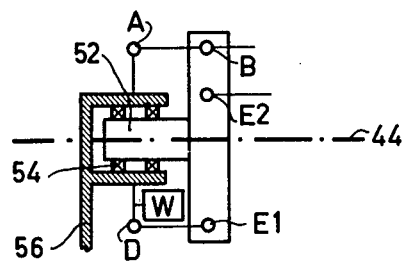

FIGS. 3a–3c schematically show different arrangements for the rotating the camera. FIG. 3a shows the supporting ring 22 of FIG. 1 with pivots B, E2 and E1 as shown in FIG. 2b supported therein. The supporting ring 22 is supported by guide wheels 38 and rotates in a bearing 50. The supporting ring 22 can be driven by means of a motor (not shown); but due to the efficient balancing and suspension, its displacement requires so little force that manual operation is also possible. Manual operation is usually considered very desirable by the users of apparatus of the kind to which the invention relates. A stepping motor can alternatively be used to rotate the gamma camera about the isocentric axis 44 through very accurately adjustable angles, for example, for axial tomography. The supporting ring 22 may be provided with an angular scale division on an outer side.

FIG. 3b shows an embodiment in which the supporting ring 22 comprises a shaft 52 which is rotatable in a bearing 54 in a supporting bracket 56.

FIG. 3c shows an embodiment in which the supporting ring 22 has a conical form and again comprises a shaft 52 which is rotatable in a bearing 58 in a supporting bracket 60. In the embodiment shown in FIG. 3c, the pivot E2 has been shifted back according to the arrangement shown in FIG. 2c.

It will be clear from the embodiments described that the invention has a wider field of application than use with a gamma camera as a detection element. The invention is notably suitable, however, for medical diagnostic apparatus in which radiation emitted by the patient is to be measured, because in such apparatus only a single element has to be positioned with respect to the patient. If a source and a detector, for example, an X-ray image intensifier tube have to be moved in a fixed mutual relationship with respect to the patient, such as in X-ray equipment, they can in principle act as a counterweight for one another. If both elements must be independently adjustable with respect to an object to be examined, it is advantageous to accomodate both in a parallelogram suspension system, so that the balance is not disturbed by a difference in adjustment.

In addition to diagnostic apparatus, for example for thermal irradiation, the invention can also be used in radiation therapy apparatus. In such apparatus, usually it is merely necessary to position the source with respect to the patient, and a high degree of freedom of movement and a suitably fixed irradiation direction are very important.

What is claimed is:

1. A radiological apparatus comprising:
    a supporting structure;
    a supporting arm pivotally amounted on the supporting structure at a first pivot point, said arm having first and second ends extending on opposite sides of the first pivot point;
    a radiological element pivotally mounted on the first end of the supporting arm at a second pivot point;
    a control arm having first and second ends, the first end pivotally connected to the radiological element at a third pivot point and the second end pivotally connected to the supporting structure at a fourth pivot point, straight lines connecting the first, second, third, and fourth pivot points tracing out a parallelogram; and
    a counterweight pivotally connected to the second end of the supporting arm at a fifth pivot point and pivotally connected to the supporting structure at a sixth pivot point, said counterweight having two portions pivotally connected to each other at a seventh pivot point, the first, fifth, sixth and seventh pivot points tracing out a parallelogram.

2. An apparatus as claimed in claim 1, characterized in that the supporting structure is a supporting ring which is rotatable about an isocentric axis of an object.

3. An apparatus as claimed in claim 2, characterized in that the supporting ring comprises a disc which is supported by two guide wheels in a bearing.

4. An apparatus as claimed in claim 2, characterized in that the supporting ring is shaped as a cone and is journalled in a bearing via a shaft.

5. An apparatus as claimed in claim 4, characterized in that the fourth pivot point is located in the cone of the supporting ring.

6. An apparatus as claimed in claim 5, characterized in that:
    the supporting ring is provided with an angular scale; and
    the apparatus further comprises a stepping motor for rotating the supporting ring about the axis.

* * * * *